(12) United States Patent
Cui et al.

(10) Patent No.: US 12,384,767 B2
(45) Date of Patent: Aug. 12, 2025

(54) PROBE FOR DETECTION OF CATHEPSIN ACTIVITY

(71) Applicant: University of Florida Research Foundation, Incorporated, Gainesville, FL (US)

(72) Inventors: Lina Cui, Gainesville, FL (US); Kelton Schleyer, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 568 days.

(21) Appl. No.: 17/797,884

(22) PCT Filed: Feb. 6, 2021

(86) PCT No.: PCT/US2021/016975
§ 371 (c)(1),
(2) Date: Aug. 5, 2022

(87) PCT Pub. No.: WO2021/159037
PCT Pub. Date: Aug. 12, 2021

(65) Prior Publication Data
US 2023/0104170 A1    Apr. 6, 2023

Related U.S. Application Data

(60) Provisional application No. 62/971,558, filed on Feb. 7, 2020.

(51) Int. Cl.
*C07D 409/12*   (2006.01)
*G01N 33/58*    (2006.01)

(52) U.S. Cl.
CPC ......... *C07D 409/12* (2013.01); *G01N 33/582* (2013.01)

(58) Field of Classification Search
CPC .................. C07D 409/12; G01N 33/582
See application file for complete search history.

(56) References Cited

U.S. PATENT DOCUMENTS 9,180,209 B2    11/2015  Bogyo et al.
2015/0337286 A1  11/2015  Kumar et al.

OTHER PUBLICATIONS

International Search Report and Written Opinion mailed Apr. 7, 2021 for Application No. PCT/US2021/016975.
International Preliminary report on Patentability mailed Aug. 18, 2022 for Application No. PCT/US2021/016975.
[No Author] Substance Record for SID 172097286. PUBCHEM. Modified Oct. 6, 2015; retrieved on Mar. 21, 2021; https://pubchem.ncbi.nlm.nih.gov/substance/172097286.
Schleyer et al., Internally Quenched Fluorogenic Probe Provides Selective and Rapid Detection of Cathepsin L Activity. BioRxIV Mar. 29, 2020. doi: 10.1101/2020.03.28.012708. Preprint. 4 pages.

*Primary Examiner* — Alicia L Otton
(74) *Attorney, Agent, or Firm* — Wolf, Greenfield & Sacks, P.C.

(57) ABSTRACT

In this vein, we present CTLAP, a fluorogenic probe that is rapidly activated by CTL and displays good selectivity over CTB and CTV, the closest competing analytes for CTL activity probes. CTLAP exhibits intrinsically low background fluorescence, which we attribute to the notably low quantum yield measured for the probe. CTLAP demonstrates markedly higher turn-on ratios (24-fold) and moderately improved enzyme selectivity (6- to 10-fold) when compared to Z-FR-AMC (10-fold turn-on ratio, 6- to 7-fold selectivity), a commercially available CTL-selective probe commonly used to detect CTL activity in mixed samples. Optimum selectivity for CTL is achieved within 10 min of incubation with the enzyme, suggesting that CTLAP is amenable for rapid detection of CTL, even in the presence of competing cathepsins.

15 Claims, 9 Drawing Sheets

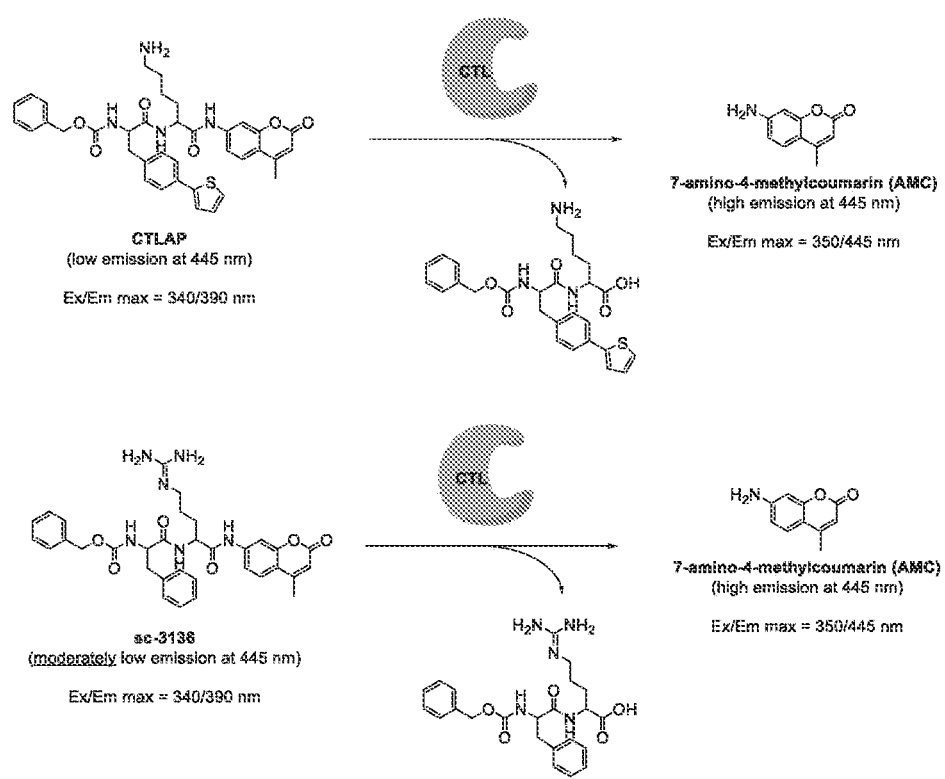
Figure 1. Activation of CTLAP and sc-3136 by CTL to generate the AMC reporter.

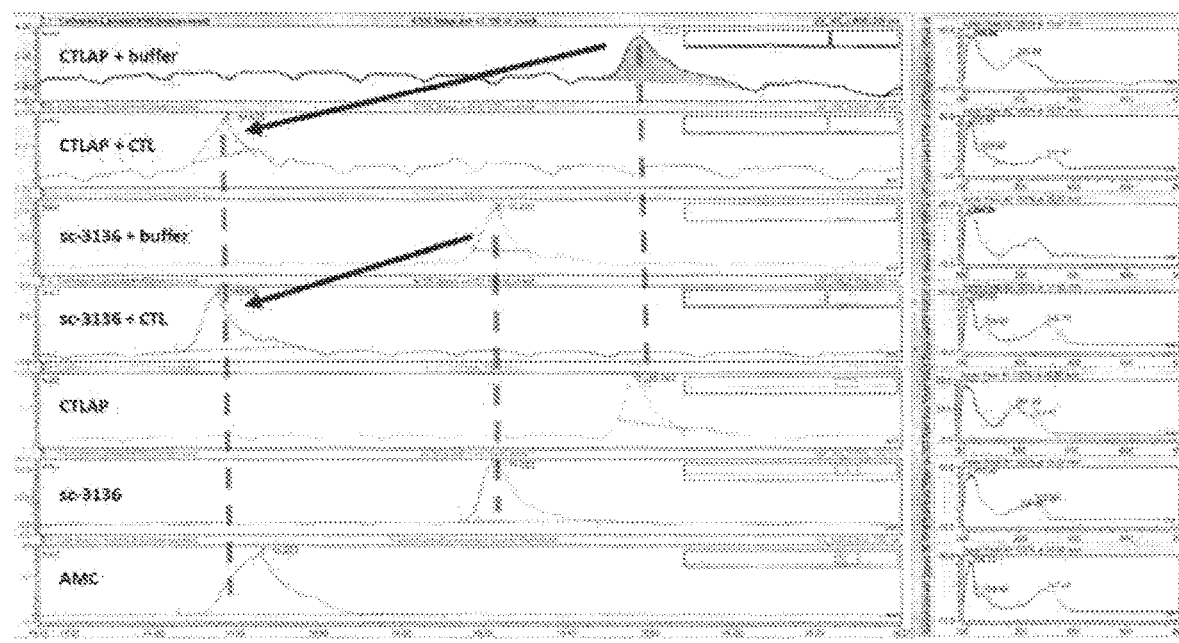
Figure 2. HPLC analysis of CTLAP and sc-3136 incubated in buffer with or without CTL.

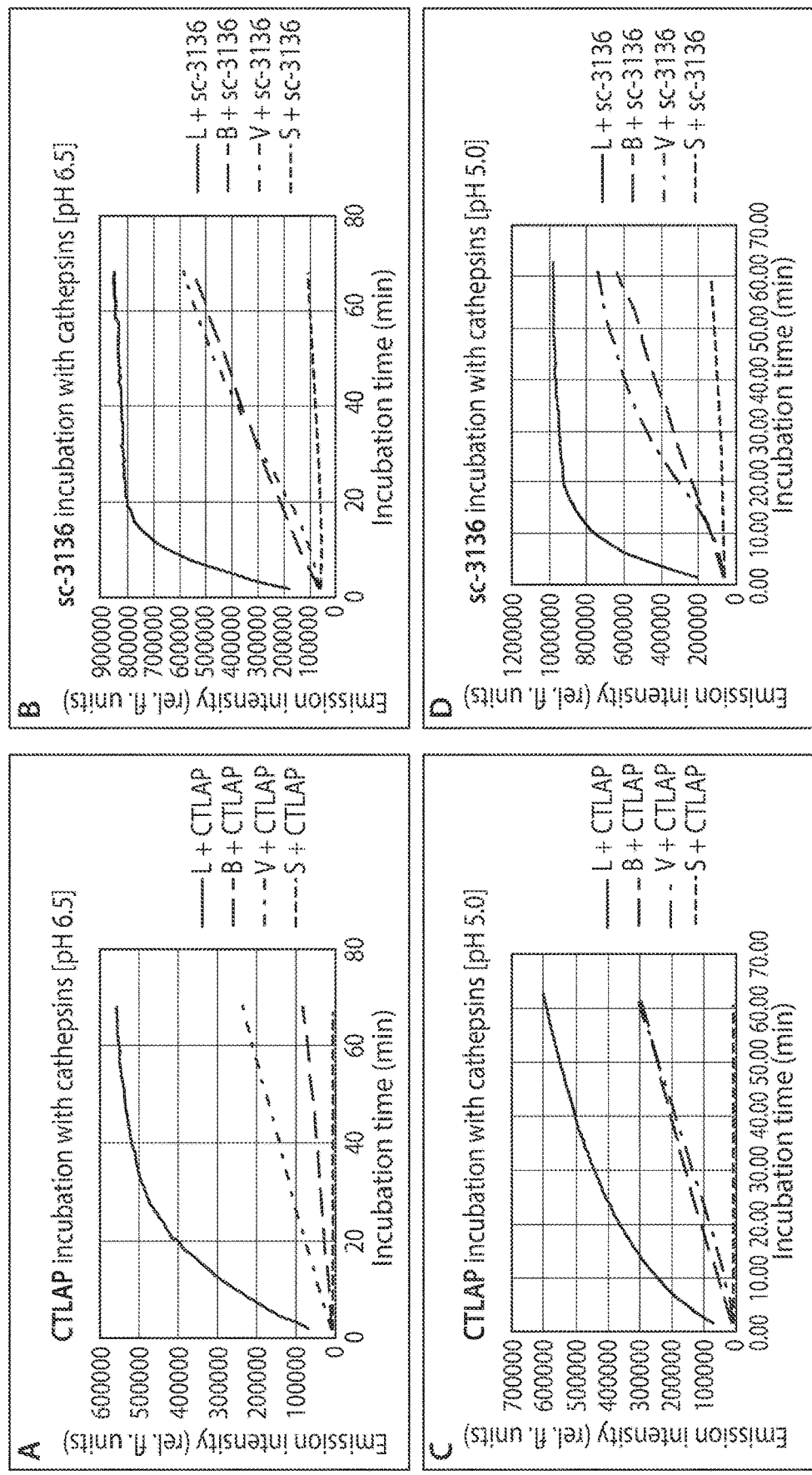
Figure 3. Time-course assay of CTLAP (A, C) and sc-3136 (B, D) with CTL, CTB, CTV, and CTS, at pH 6.5 (A, C) or 5.0 (B, D).

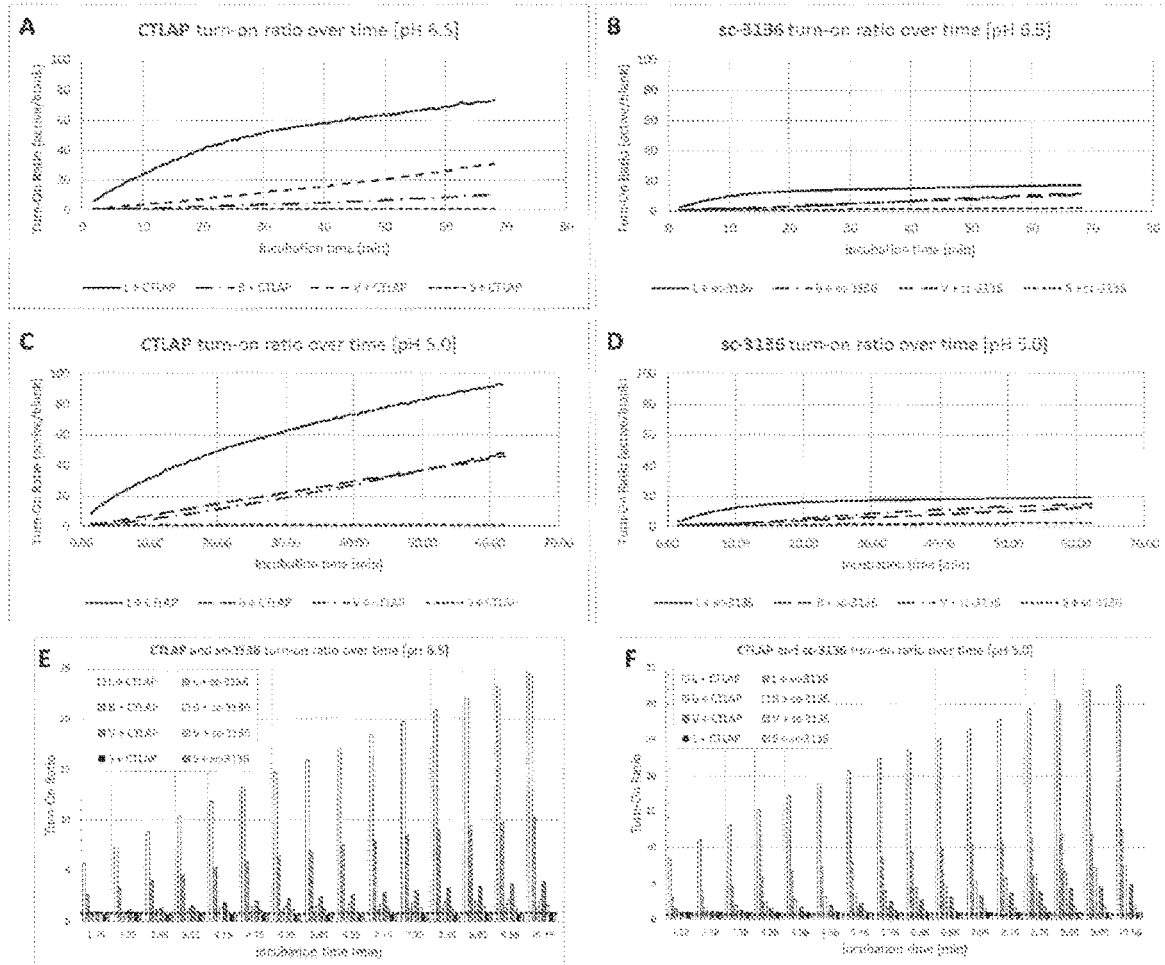
Figure 4. Turn-on ratio for CTLAP (left) or sc-3136 (right) at pH 6.5 (A, C) and 5.0 (B, D). The turn-on ratios of all enzyme-probe pairs for first 10 min of incubation is shown at pH 6.5 (E) and 5.0 (F). In each grouping of eight bars at a time point, the plots are L+CTLAP, L+sc-3136, B+CTLAP, B+sc-3136, V+CTLAP, V+sc-3136, S+CTLAP, and S+sc-3136, from left to right along the X-axis, respectively.

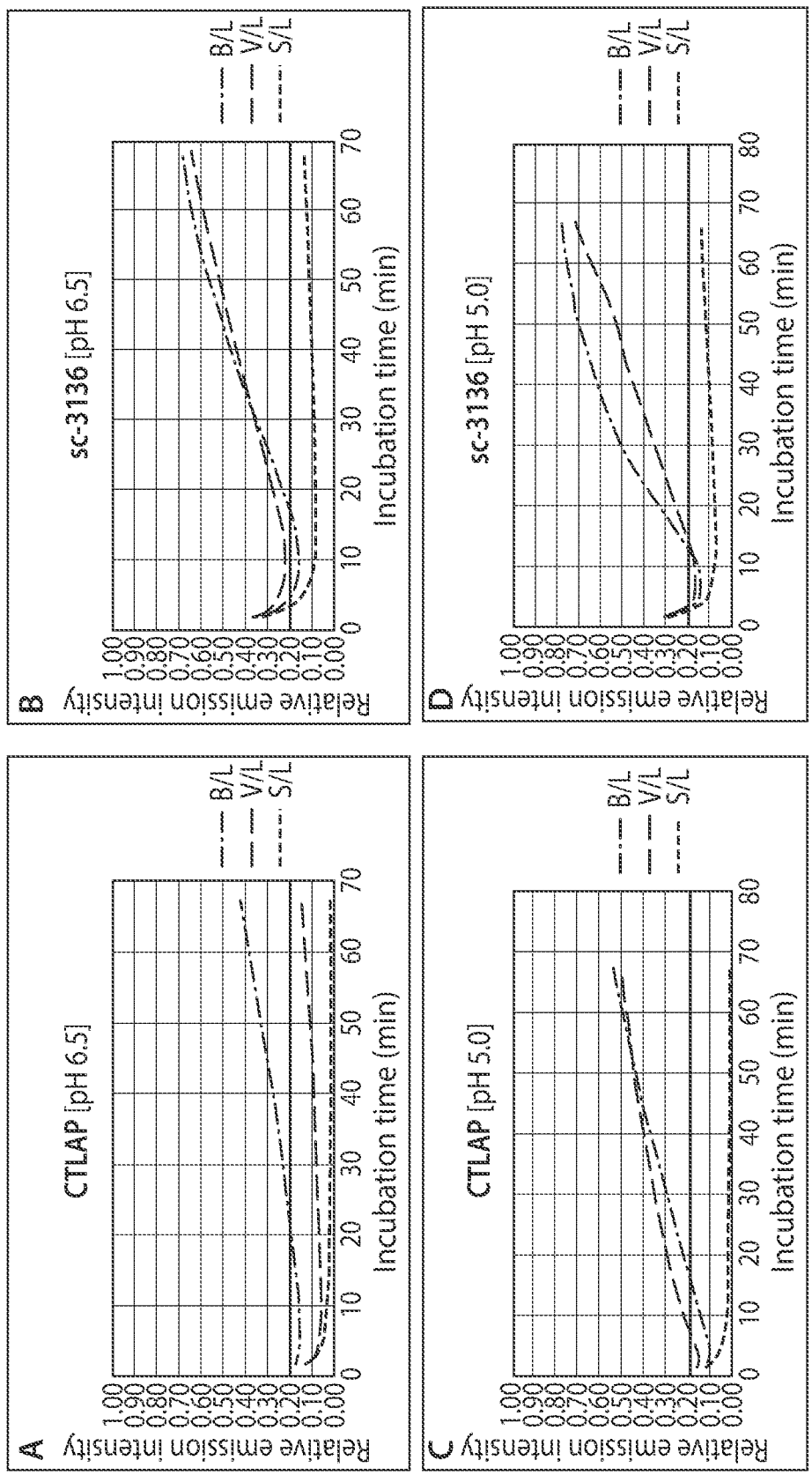
*Figure 5.* Signal generated from CTLAP (left) and sc-3136 (right) activation by off-target cathepsins B, V, and S, normalized against that produced by CTL. Data is shown for pH 5.0 (A, C) and 6.5 (B, D). The solid line indicates the 0.20 mark, or 20% signal relative to CTL.

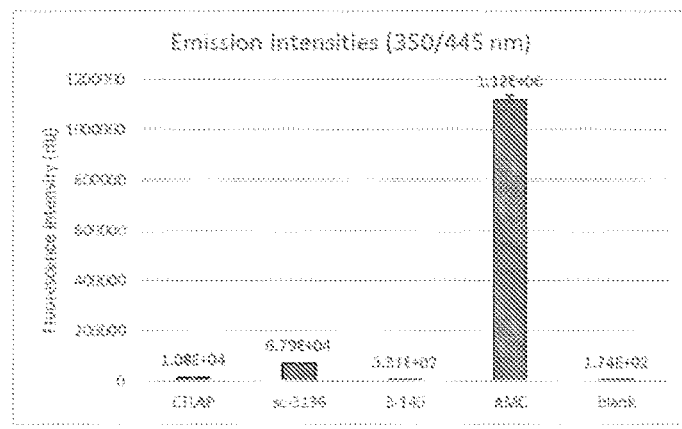
Figure 6. Emission intensity of 5 μM compounds (350 nm excitation, 445 nm emission). Blank is a buffer blank containing no compounds. Error bars are S.D. of three replicates.
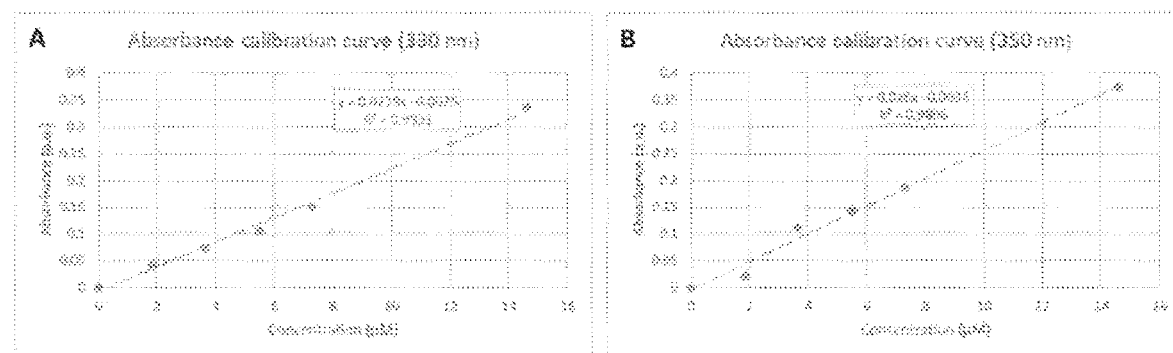
Figure 7. Calibration curves of CTLAP absorbance between 0 μM and 16 μM in cathepsin reaction buffer, pH 5.0. Absorbance was measured at 330 nm (a) and 350 nm (b).

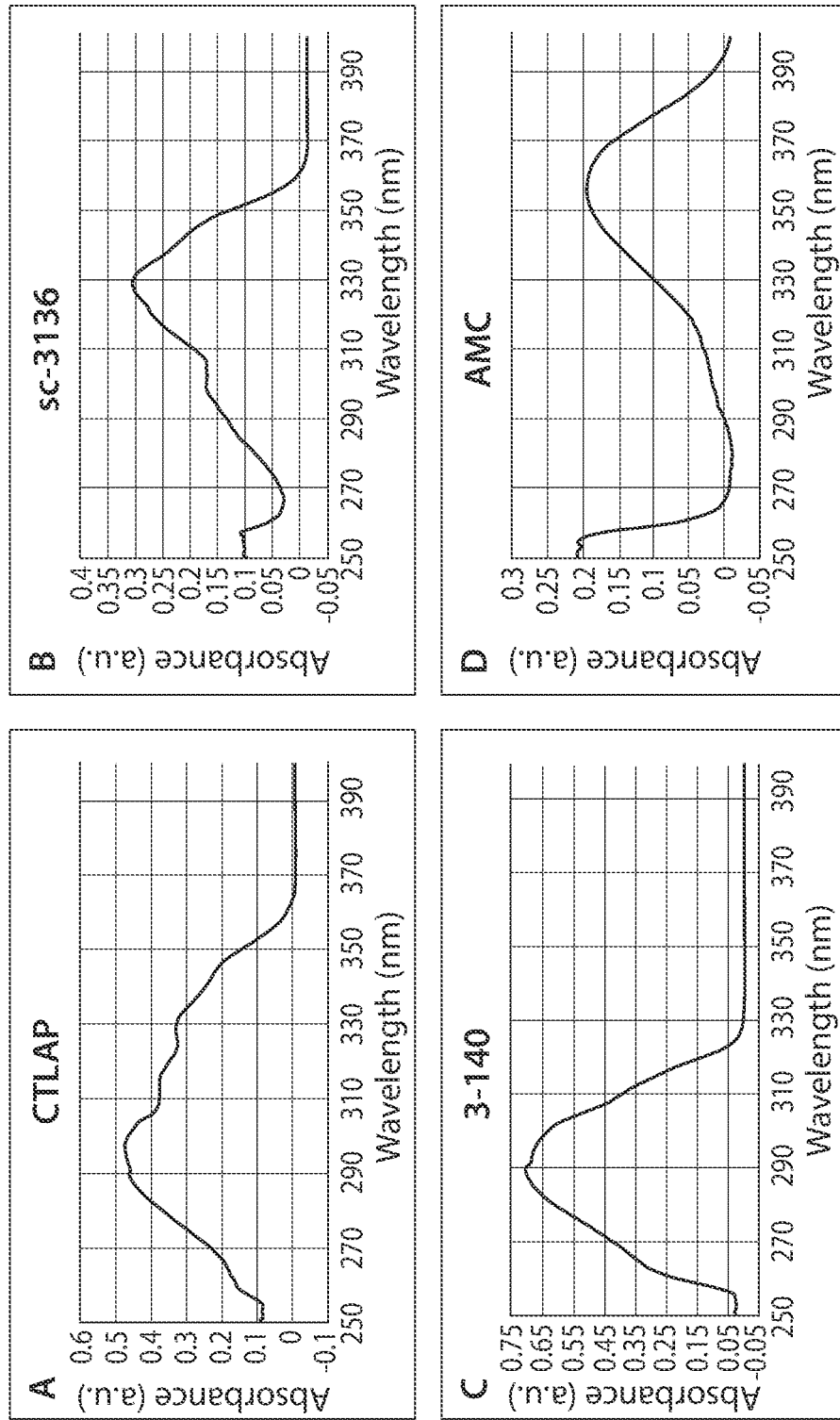
Figure 8. UV-vis absorption spectra of CTLAP (A), sc-3136 (B), 3-140 (C), and AMC (D) in DMSO.

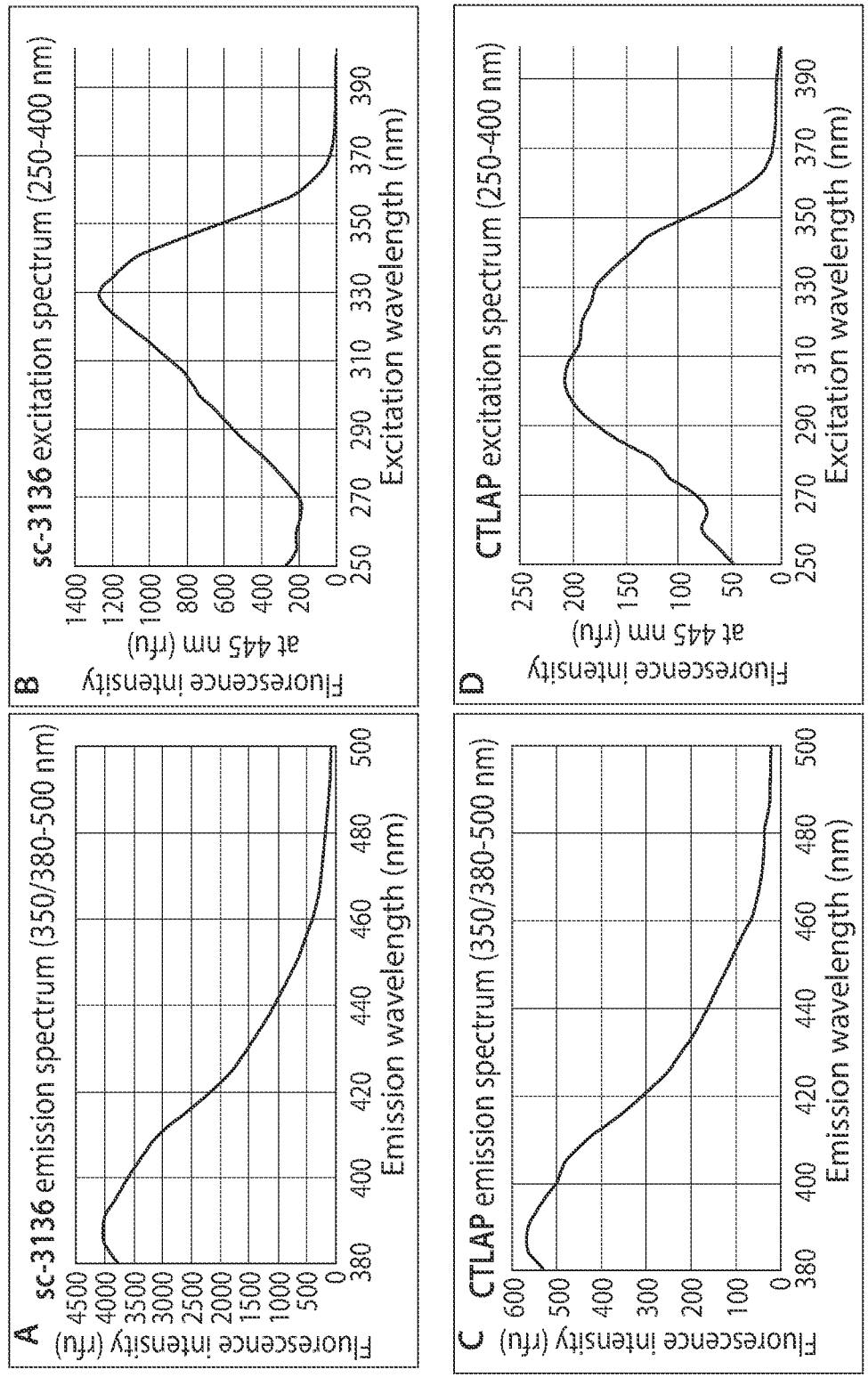
Figure 9. Emission (left) and excitation (right) spectra of sc-3136 (A, B) and CTLAP (C, D). Emission spectra collected at excitation 350 nm, emission 380-500 nm. Excitation spectra were collected at excitation 250-400 nm, emission 445 nm.

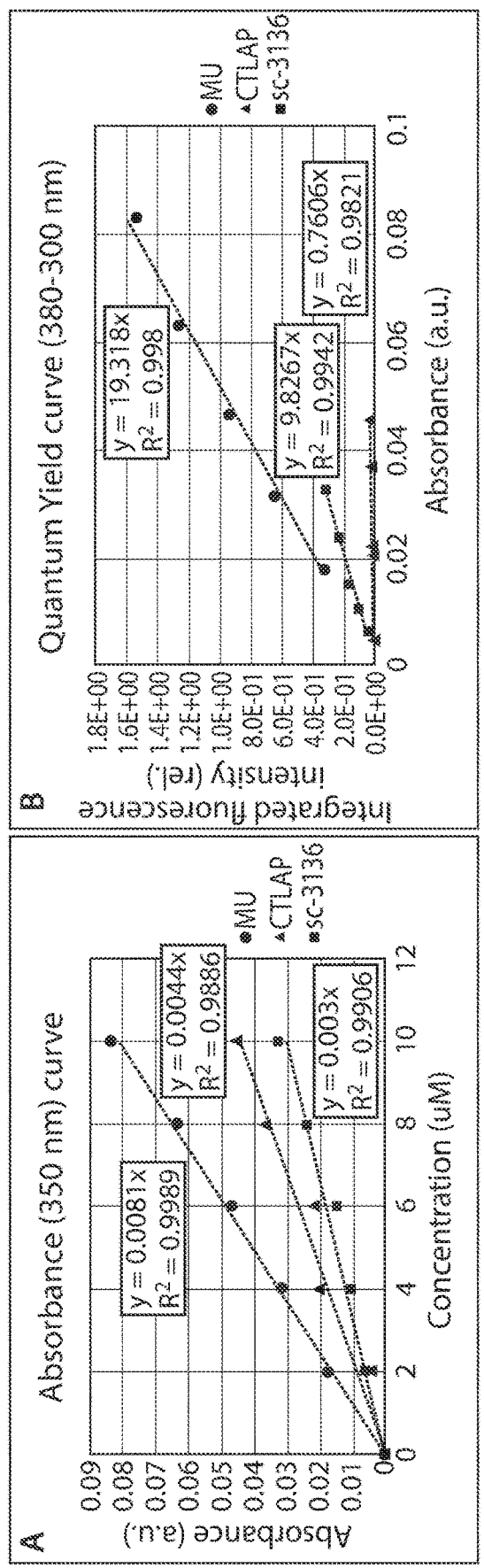
Figure 10. Measurement of molar attenuation coefficient (A) and quantum yield (B) for CTLAP (triangle) and sc-3136 (square). Values were standardized against 4-methylumbelliferone (MU, circle). The slope and fit of the linear trendline are shown in boxes of the respective plot.

PROBE FOR DETECTION OF CATHEPSIN ACTIVITY

CROSS-REFERENCE TO RELATED APPLICATIONS

This application is a national stage filing under 35 U.S.C. § 371 of International Patent Application Serial No. PCT/US2021/016975, filed Feb. 6, 2021, which claims priority to U.S. application 62/971,558, filed Feb. 7, 2020, the entire contents of each of which are hereby incorporated herein by reference.

STATEMENT OF GOVERNMENT SUPPORT

This invention was made with government support under GM124963 awarded by the National Institutes of Health. The government has certain rights in the invention.

BACKGROUND

Herein, structure-defined cathepsin probes for selective cathepsin detection are described.

The cathepsin family of lysosomal proteases includes up to 16 members, distributed in unique patterns among different tissue types[1]. Most are cysteine proteases active at low pH, optimal for lysosomal activity. Some members are tightly connected in activity, and knockout mice missing even one cathepsin show very poor survival[2].

Cathepsins are upregulated in all tumor-related cells, although certain family members tend to be distributed in different cell types[3]. Cathepsin L (CTL) is observed in fibroblasts, TAMs, myoepithelial cells, endothelial cells, and tumor cells[4]. Cathepsin localization to the mitochondria is accomplished by post-translational addition of a mannose-6-phosphate glycan; in cancers it is possible that cathepsins are selectively re-routed (or m-6-pylation is attenuated in general) and as a result these enzymes are exocytosed and are partially active in the semi-acidic pH of the tumor ECM[2,5].

Of the cathepsin family, CTL is the only enzyme known to process pro-heparanase and generate active heparanase[6], a carbohydrate-processing enzyme associated with extracellular matrix (ECM) remodeling[7]. CTL itself is associated with ECM degradation and tumor invasion, indicating that this enzyme both actively participates in tumor aggression and also promotes an aggressive phenotype in activating other ECM-degrading enzymes[1]. For CTL, the standard fluorogenic probe used to selectively detect activity is Z-FR-AMC, a commercially available dipeptide probe (Catalog #sc-3136, Santa Cruz Biotechnology). The chemical structure of Z-FR-AMC includes phenylalanine, arginine, and carboxybenzyl (Cbz, or Z) moieties which provide selectivity for CTL over other enzymes; however, this probe still exhibits activation by CTB and CTV, homologues of CTL. While CTV is isolated to a handful of tissues in the human body, CTB is widely expressed, often concomitantly with CTL. Thus, off-target detection of CTB by Z-FR-AMC could confound assay results. In fluorogenic assays, the presence of high background emission reduces the sensitivity of the method. A fluorogenic compound with low background would thus provide better sensitivity for fluorogenic detection of cathepsin L activity.

Described herein is the discovery of CTLAP, a fluorogenic probe exhibiting both selectivity for CTL over other cathepsins (6- to 10-fold), and a low background intensity compared to a commercial standard probe (sc-3136), providing a 24-fold increase in emission intensity within 10 min of incubation with CTL. The chemical structure of CTLAP facilitates both of these benefits, a pattern not observed previously in the literature.

BRIEF SUMMARY OF THE INVENTION

In some aspects, the invention is directed toward compounds that interact with cathepsins, uses in cathepsin inhibitor screening, methods of synthesis, methods of modulating cathepsin activity, methods of detecting and measuring cathepsin, and methods of treating disease and disorders associated with cathepsin. In some aspects, provided herein are compounds for use in treating one or more diseases or disorders associated with the function of cathepsin. The compounds can be used to test cathepsin L activity in vitro. The compounds and methods described herein are useful research tools to study biology related to cathepsins, as well as screening of cathepsin inhibitors. Also described is use of the compounds as part of a kit to evaluate clinical samples for diagnostic and prognostic purposes.

In one aspect, the invention is directed to a compound of any of the formulae herein, or a salt thereof.

In one aspect, the invention is directed to a compound CTLAP (describe herein), or a salt thereof.

In another aspect, the invention is directed to a composition comprising a compound of any of the formulae presented herein, or a salt thereof.

In another aspect, the invention is directed to a composition comprising CTLAP, or a salt thereof.

In another aspect, the invention is a method for screening for cathepsin inhibitors, the method comprising:
a. incubating cathepsin with a test compound;
b. adding a compound of any of the formulae herein (e.g., CTLAP), or a salt thereof;
and
c. measuring the fluorescence of the mixture from step b.

In another aspect, the invention is a method wherein the cathepsin is cathepsin L.

In another aspect, the invention is a method further comprising plotting the fluorescence from step c.

In another aspect, the invention is a method further comprising plotting the fluorescence from step c, wherein the cathepsin is cathepsin L.

In another aspect, the invention is a method for screening for cathepsin inhibitors, the method comprising:
a. combining cathepsin, a test compound, and a compound of any of the formulae herein (e.g., CTLAP), or a salt thereof; and
b. measuring the fluorescence of the mixture from step a.

In another aspect, the invention is a method wherein the cathepsin is cathepsin L.

In another aspect, the invention is a method further comprising plotting the fluorescence from step b.

In another aspect, the invention is a method further comprising plotting the fluorescence from step b, wherein the cathepsin is cathepsin L.

In another aspect, the invention is a kit comprising a compound of any of the formulae herein (e.g., CTLAP), or a salt thereof, and instructions for screening test compounds. The kit can further comprising one or more buffers.

In another aspect, the invention is a kit comprising a compound of any of the formulae herein (e.g., CTLAP), or a salt thereof, and instructions for screening clinical samples. The kit can further comprising one or more buffers.

In another aspect, the invention is a method for screening clinical samples, the method comprising:

a. providing a clinical sample;
b. combining the sample with a compound of any of the formulae herein (e.g., CTLAP), or a salt thereof; and
c. measuring the fluorescence of the mixture from step b.

The sample can be urine, saliva, or blood. The method can further comprise combining an inhibitor of cathepsin B, V or S.

In another aspect, the invention is method for screening clinical samples, the method comprising:
a. combining the clinical sample and a compound of any of the formulae herein (e.g., CTLAP), or a salt thereof; and
b. measuring the fluorescence of the mixture from step a.

The sample can be urine, saliva, or blood. The method can further comprise combining an inhibitor of cathepsin B, V or S.

The details of one or more embodiments of the invention are set forth in the accompanying Figures, the Detailed Description, and the Examples. Other features, objects, and advantages of the invention will be apparent from the description and the claims.

BRIEF DESCRIPTION OF THE DRAWINGS

The present invention is further described below with reference to the following non-limiting examples and with reference to the following figures, in which:

FIG. 1 shows Activation of CTLAP and sc-3136 by CTL to generate the AMC reporter.

FIG. 2 shows HPLC analysis of CTLAP and sc-3136 incubated in buffer with or without CTL.

FIG. 3 shows Time-course assay of CTLAP (A, C) and sc-3136 (B, D) with CTL, CTB, CTV, and CTS, at pH 6.5 (A, C) or 5.0 (B, D).

FIG. 4 shows Turn-on ratio for CTLAP (left) or sc-3136 (right) at pH 6.5 (A, C) and 5.0 (B, D). The turn-on ratios of all enzyme-probe pairs for first 10 min of incubation is shown at pH 6.5 (E) and 5.0 (F). In each grouping of eight bars at a time point, the plots are L+CTLAP, L+sc-3136, B+CTLAP, B+sc-3136, V+CTLAP, V+sc-3136, S+CTLAP, and S+sc-3136, from left to right along the X-axis, respectively.

FIG. 5 shows Signal generated from CTLAP (left) and sc-3136 (right) activation by off-target cathepsins B, V, and S, normalized against that produced by CTL. Data is shown for pH 5.0 (A, C) and 6.5 (B, D). The solid dashed line indicates the 0.20 mark, or 20% signal relative to CTL.

FIG. 6 shows Emission intensity of 5 µM compounds (350 nm excitation, 445 nm emission). Blank is a buffer blank containing no compounds. Error bars are S.D. of three replicates.

FIG. 7 shows Calibration curves of CTLAP absorbance between 0 µM and 16 µM in cathepsin reaction buffer, pH 5.0. Absorbance was measured at 330 nm (a) and 350 nm (b).

FIG. 8 shows UV-vis absorption spectra of CTLAP (A), sc-3136 (B), 3-140 (C), and AMC (D) in DMSO.

FIG. 9 shows Emission (left) and excitation (right) spectra of sc-3136 (A, B) and CTLAP (C, D). Emission spectra collected at excitation 350 nm, emission 380-500 nm. Excitation spectra were collected at excitation 250-400 nm, emission 445 nm.

FIG. 10 shows Measurement of molar attenuation coefficient (A) and quantum yield (B) for CTLAP (triangle) and sc-3136 (square). Values were standardized against 4-methylumbelliferone (MU, circle). The slope and fit of the linear trendline are shown in boxes of the respective plot.

DEFINITIONS

Before further description of the present invention, and in order that the invention may be more readily understood, certain terms are first defined and collected here for convenience.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

Salt forms of the compounds of any of the formulae herein include inorganic and organic acid salts. Such salt forms can be made using any acidic chemical, which can be inorganic (e.g., hydrochloric, hydrobromic, sulfuric, nitric acids, aluminum trichloride) or organic (e.g., camphorsulfonic acid, p-toluenesulfonic acid, acetic acid, ytterbium triflate) in nature.

As used herein, the term "treating" a disorder encompasses ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes blocking, inhibiting, attenuating, protecting against, modulating, reversing the effects of and reducing the occurrence of e.g., the harmful effects of a disorder.

As used herein, "inhibiting" encompasses reducing and halting progression.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "protein" refers to series of amino acid residues connected one to the other by peptide bonds between the alpha-amino and carboxy groups of adjacent residues.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "screening effective amount" refers to that amount of the compound being administered sufficient to performing a screen.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents. The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, hydrobromic, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions. Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I-, Cl-, Br-, F-), hydroxy, alkoxy (e.g., -OMe, -O-t-Bu), acyloxy anions (e.g., -OAc, -OC(O)CF$_3$), sulfonates (e.g., mesyl, tosyl), acetamides (e.g., -NHC(O)Me), carbamates (e.g., N(Me)C(O)Ot-Bu), phosphonates (e.g., -OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

DETAILED DESCRIPTION OF THE INVENTION

In some aspects, the invention is directed toward compounds that interact with cathepsin, uses in cathepsin screening, methods of synthesis, methods of modulating cathepsin activity, methods of detecting cathepsin, and methods of treating disease and disorders associated with cathepsin. In some aspects, provided herein are compounds for use in treating one or more diseases or disorders associated with the function of cathepsin, including detection of cathepsin. The term "cathepsin" refers to one or more of a family of protease enzymes known in the art and including but not limited to cathepsin A, B, C, D, E, F, G, H, K, L, L1 (or L), L2 (or V), O, S, W, or Z (or X).

In another aspect, the invention is directed to a kit comprising a compound of any of the formulae presented herein, or a salt thereof, and instructions for screening for cathepsin inhibitors.

The compounds of the formulae herein (e.g., CTLAP or salt thereof) can be used to test cathepsin (e.g., cathepsin L) activity in vitro. The compounds and methods herein provide a very useful research tool to study biology related to cathepsins, as well as for screening of cathepsin inhibitors. For biological study, the probe is added directly to the sample in a vial or plate, and a fluorescence signal can be read directly using a fluorometer or plate reader. For inhibitor screening, the probe is incubated together with cathepsin and a test compound. Inhibition of the cathepsin by the test compound gives a reduction in fluorescence signal, thereby determining the inhibitory efficiency of the test compound.

The compounds of the formulae herein (e.g., CTLAP or salt thereof) can be included into a kit to evaluate clinical samples for diagnostic and prognostic purposes. The kit includes a compound of any of the formulae herein (e.g., CTLAP or salt thereof), buffer, and optionally inhibitors of other cathep sins. For example, if it desired to achieve an extremely high cathepsin L selective signal, inhibitors for cathepsin B, V, or S, could also be used in the kit and methods to further enhance the selectivity. For such application, clinical samples (including but not limited to urine, saliva, blood) from patients (including but not limited to cancer patients) are collected, and then incubated with components of the kit. Fluorescent readout will indicate whether specific cathepsin(s) is present in the patient samples. The result can be correlated with other diagnostic indices of the patient to validate the relationship of the test results and disease progression.

Compounds delineated herein include salts, hydrates, solvates, and prodrugs thereof. In certain embodiments, compounds delineated herein include hydrate and solvates thereof. Compounds described herein may be derivatized to produce a salt form or prodrug form that may be more useful in one or more of the procedures and/or methods (e.g., methods of treatment) described herein. All compounds delineated in schemes herein are contemplated and included, whether intermediate or final compounds in a process.

Compounds of the invention can be made or modified by means known in the art of organic synthesis. Methods for optimizing reaction conditions, if necessary minimizing competing by-products, are known in the art. Additional reaction schemes, optimization, scale-up, and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The details of one or more embodiments of the invention are set forth in the accompanying Figures, the Detailed Description, and the Examples. Other features, objects, and advantages of the invention will be apparent from the description and the claims.

A. Design and Synthesis of Fluorogenic Cathepsin L Probe, CTLAP

We designed CTLAP based on the known substrate preferences of CTL[8,9]. The enzyme accepts non-polar or basic residues in the P1 position, so we selected lysine due to its simpler synthesis over arginine. The P2 position demonstrates preference for aromatic and non-polar residues, with greater selectivity being afforded by extended aromatic residues such as the benzyl-thiophene group[10]. The P3 residue is generally occupied well by a Cbz protecting group, although not much selectivity is conferred by this substituent. In selecting a reporter, 7-amino-4-methylcoumarin (AMC) is a standard dye used for fluorogenic cathepsin probes. A linker between the AMC fluorophore and the peptide scaffold was excluded, as previous work has demonstrated that such linkers tend to shift probe selectivity in favor of CTB and away from CTL, working against the design goals for this probe[11].

The probe was synthesized according to Scheme 1. Amide coupling between the AMC amine and Fmoc-Lys(Boc)-OH was accomplished using phosphoryl chloride with pyridine in anhydrous tetrahydrofuran. The Fmoc group was removed in a 5% solution of piperidine in DMF at room temperature for 5 min. The Cbz-protected 4-(2-thiophene)-phenylalanine was synthesized by first mixing a suspension of 4-iodophenylalanine with benzyl chloroformate in the presence of potassium carbonate in toluene and water at room temperature for 22 h, then performing a Suzuki coupling reaction between the 4-iodo position and thiophene-2-boronic acid. This modified amino acid was then coupled with the de-blocked Lys(Boc)-AMC intermediate to complete the peptide scaffold, using HBTU, HOBt, and DIPEA in DMF at room temperature for 30 min. The Boc group was removed using a 20% solution of trifluoroacetic acid in DCM in the presence of triisopropylsilane at room temperature for 30 min. The final product CTLAP was purified by HPLC.

Scheme 1. Synthetic scheme of target compound, CTLAP.

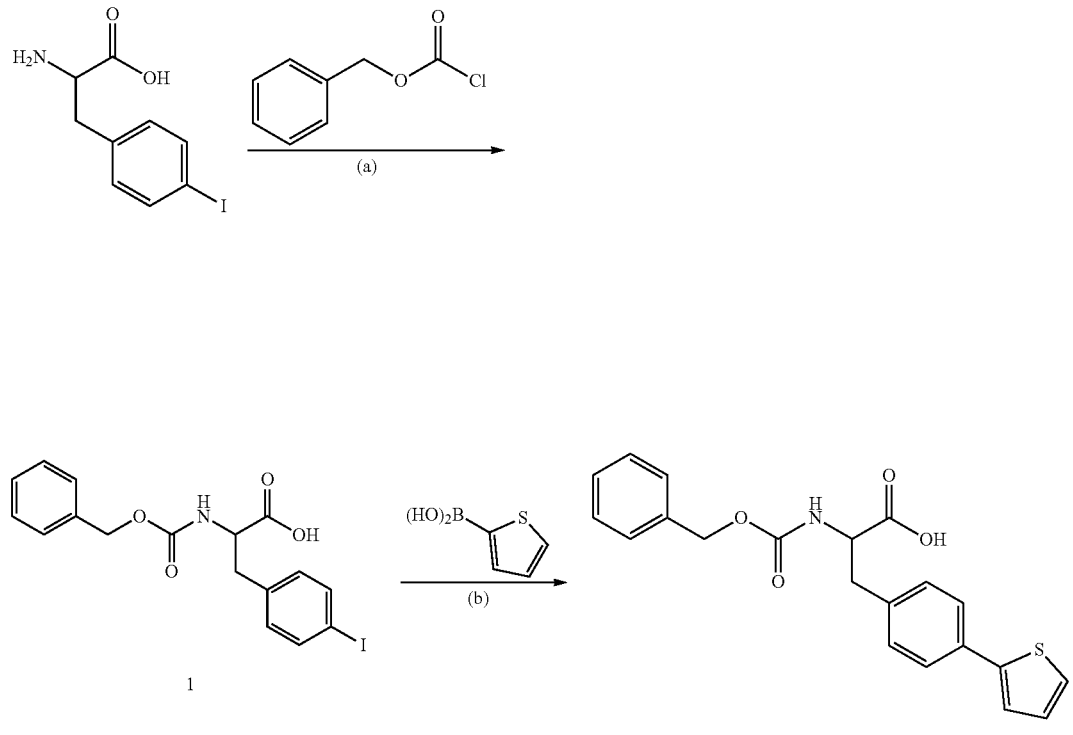

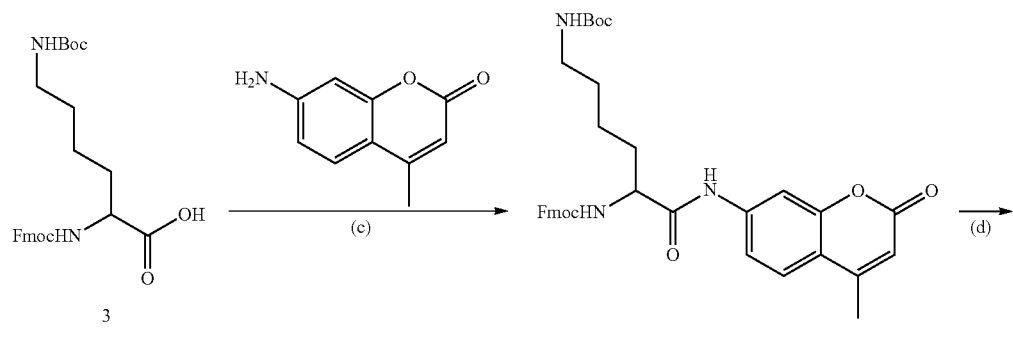
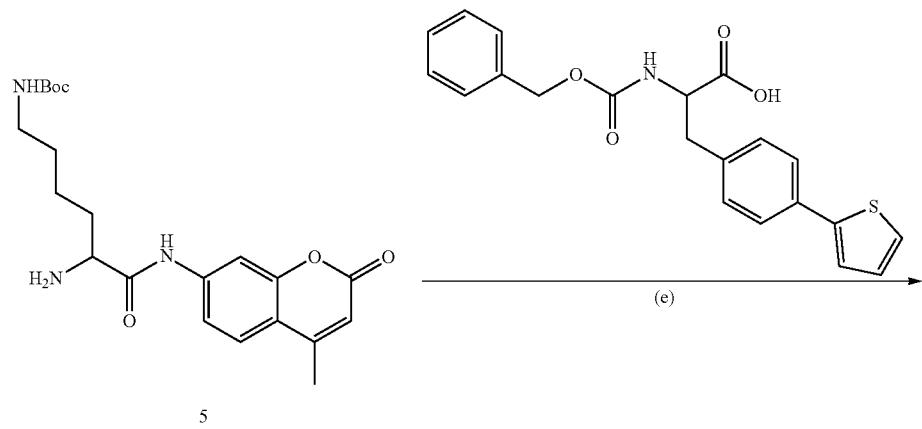
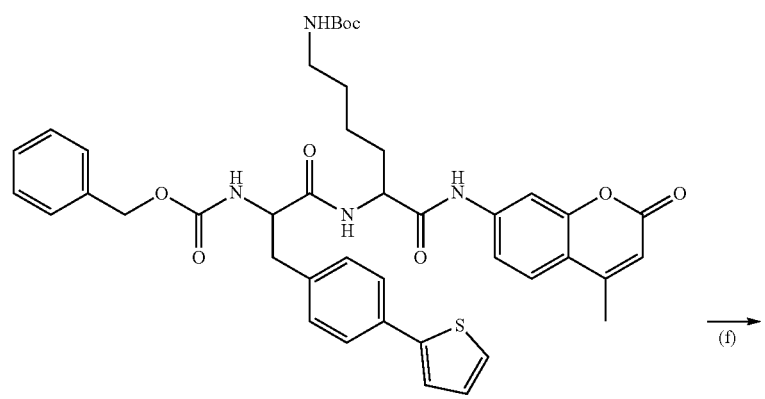

-continued

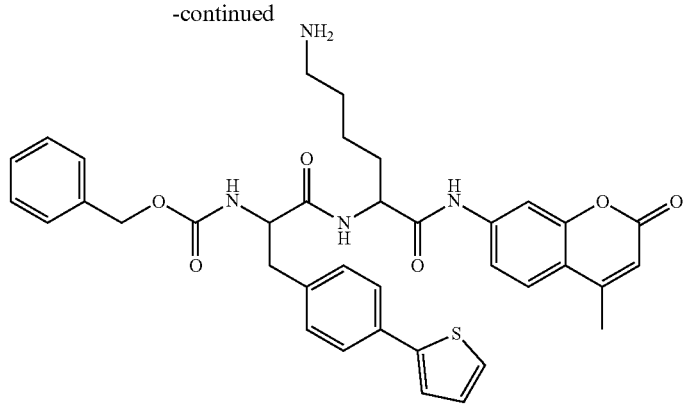

CTLAP

Reagents and conditions: (a) benzyl chloroformate, $K_2CO_3$, toluene, $H_2O$, 0° C. -> r.t., 22 h, 82%; (b) thiophene-2-boronic acid, $Pd(PPh_3)_4$, $K_2CO_3$, $MeCN/H_2O$ (3:1), 80° C., OVN, 56%; (c) 7-amino-4-methylcoumarin (AMC), $POCl_3$, pyridine, THF (anhydrous), 0° C., 1.5 h; (d) 5% piperidine/DMF, r.t., 5 min, 65%; (e) Z-Phe(thiophene)-OH, HBTU, HOBt, DIPEA, DMF (anhydrous), r.t., 30 min; (f) 20% TFA/DCM, triisopropylsilane, r.t., 30 min, quantitative (HPLC).

CTLAP was examined for its capacity to be activated by CTL, its selectivity for CTL over similar cathepsins, and its emission properties. For comparison, Z-FR-AMC (sc-3136) was purchased and used in all experiments. Also, the benzyl-thiophene amino acid synthetic intermediate (3-140) was examined as well as the free AMC fluorophore when comparisons were deemed insightful (FIG. 1).

B. Selectivity of CTLAP for CTL Over Competing Cathepsins

Processing of CTLAP by CTL

To confirm recognition of CTLAP by CTL, the probe was incubated with CTL in buffer at pH 5.0, and the probe was examined by HPLC analysis (FIG. 2). The compound alone in buffer retained maximum absorption at 330 nm. When incubated with CTL, the probe excitation and emission values were red-shifted, with excitation shifting to 350 nm and emission shifting to 445 nm; HPLC analysis indicated full conversion to a more-polar peak ($t_R$=14.5 min) with retention time similar to that of free AMC dye ($t_R$=14.6 min), and a novel UV spectrum with a maximum at 347 nm, consistent with the spectrum of AMC. The data is consistent with that of sc-3136, which undergoes the same reaction with CTL and generates the same free AMC product, indicating that CTLAP is recognized by CTL and converted to the fluorescent AMC reporter.

Time-Course Cathepsin Assay With 3-157 and sc-3136

To examine the selectivity of CTLAP for CTL, the probe was incubated with CTL, CTB, CTV, or CTS in buffer at pH 6.5 (near-optimal for CTL activity)[12], and emission intensity of liberated AMC was measured over the first hour of incubation (FIG. 3A). The kinetic curves have markedly different shapes for each enzyme, with CTL being the only enzyme exhibiting a plateau within 1 h. CTV and CTB appear to remain within the initial velocity region of the curves during this time, with a markedly lower slope than that observed for CTL initially. For sc-3136 (FIG. 3B), this same trend is observed, however the initial velocities of CTV and CTB have equal magnitude and are more comparable to the signal of CTL. The initial velocity of sc-3136 with CTL is higher than with CTLAP; while sc-3136 exhibits a faster initial velocity than CTLAP with CTL, this trend is also observed for CTB and CTV, resulting in overall lower selectivity for CTL compared to CTLAP.

The kinetic assays were repeated at pH 5.0 (FIG. 3C, D), and overall the same trends were observed as at pH 6.5. One notable difference is the altered reaction slope of CTL at this pH, which appears to have less of a plateau and instead seems to shift to a second phase of constant, yet slower, velocity. This is sensible, as CTL is less active at the lower pH of 5.0 (ref. 6). Also, at this pH CTB demonstrates a faster initial velocity, identical to that of CTV. This results in higher signal generation by CTB, and therefore greater off-target signal in an assay for CTL activity. This improved activity of CTB at low pH is consistent with previous observations that CTB's unique carboxypeptidase activity is dependent on an acidic environment, and that this activity is disengaged at neutral pH[13].

To determine the relative selectivity of either probe for CTL, we examined the turn-on ratio (TOR) of the probes in response to each enzyme over the first hour of incubation by dividing the emission intensity at each time point by the average intensity of the probe in buffer without enzyme (FIG. 4). This reveals the relative increase in readout signal generated by each enzyme over time. In each graph the trend is identical to that seen in FIG. 3; however, comparison of CTLAP (FIG. 4A, C) to sc-3136 (FIG. 4B, D) reveals a dramatic difference in TOR between the two probes, with CTLAP achieving a TOR approximately 4-fold greater than that of sc-3136 after 1 h incubation. This suggests that CTLAP has the capacity for greater sensitivity in detecting CTL activity.

To estimate relative selectivity of the compounds for CTL over the other enzymes, the intensity at each time point for CTB, CTV, or CTS, was divided by the intensity of CTL at the same time point; this normalizes CTL-generated signal intensity to 1.0, and expresses the relative signal generated by the other enzymes (FIG. 5). These graphs indicate that off-target signal is least prominent within the first 10 min of incubation, as the faster kinetics of the probes to CTL generate more contrast at these earlier time points. To quantify the selectivity of CTLAP and sc-3136, the lowest interfering signal from each enzyme was identified and tabulated in Table 1. Also identified was the assay time at which the total competing signal (sum of CTB, CTV, and CTS) was lowest, and the relative intensity of all competing enzymes at that time point. As seen in Table 1, CTLAP reports lower off-target signaling at all time points across the first hour of incubation, at both pH 5.0 and 6.5; the conditions exhibiting the lowest interferences are 10.2-10.4 min incubation time at pH 6.5. These results indicate that CTLAP has greater selectivity for CTL sc-3136, generating lower off-target signal. The optimum results are achieved within 10 min incubation time, lending strength to the application of CTLAP for rapid detection of CTL, even in the presence of competing enzymes.

TABLE 1

Optimal cathepsin signal normalized to CTL

|  | CTLAP | | sc-3136 | |
| --- | --- | --- | --- | --- |
| pH | 5.0 | 6.5 | 5.0 | 6.5 |
| CTB | 15% | 6% | 16% | 21% |
| CTV | 10% | 15% | 14% | 16% |
| CTS | 1% | 1% | 7% | 7% |
| B + V + 5 | 31% | 25% | 39% | 46% |
| time (min) | 3.4-4.0 | 10.2-11.4 | 7.6 | 11.4 |

Table 1. Signal generated by CTB, CTV, and CTS, or all three enzymes together, relative to CTL signal at that time point. The lowest competing signal over the time course in FIG. 5 was selected for each individual enzyme, as well as for the sum of signals from all three enzymes. The time point at which the sum of all competing signals is lowest is also listed.

C. CTLAP Exhibits Reduced Background Signal, Quantum Yield

As seen in FIG. 4, CTLAP consistently reported a higher TOR than sc-3136 under all assay conditions. This is attributed to the lower emission intensity observed in CTLAP in buffer without enzyme; the measured emission intensity of the compound at 5 µM is consistently 6- to 8-fold lower than that of sc-3136 (FIG. 6). As low background signal can improve the sensitivity and detection limit of fluorogenic assays, we sought to identify the cause of the low background intensity of CTLAP. We first examined the spectral and photophysical properties of the compound to confirm that this low background intensity was not an artifact of experimental methods. Our results indicate that CTLAP has a quantum yield significantly lower than that of sc-3136, causing the 6-to-8-fold reduction in background signal and greater TORs observed in the experiments described above. CTLAP Absorbance has Linear Relationship With Concentration Near Assay Concentration In our assays the working concentration of the compounds was calculated using a calibration curve of the compound absorbance at 330 nm, across the concentration range tested. The emission intensity was measured under assay conditions (cathepsin reaction buffer, pH 5.0) at 350 nm excitation, 445 nm emission wavelengths. The observed lower background intensity for CTLAP could be explained by three hypotheses: (1) the absorbance values used in calibrating the compound stock concentration were inaccurate; (2) the measured emission intensities of the compounds were inaccurate, reporting a consistently higher value for CTLAP in spite of the compound being at equal concentration to that of sc-3136; (3) the quantum yield of CTLAP is lower than that of sc-3136, resulting in lower emission intensity at equal concentration.

We first examined hypothesis (1), that the absorbance values of CTLAP are inaccurate and result in a lower true concentration of probe used in these assays. We first determined whether absorbance of CTLAP and sc-3136 was linear near the concentration used in the enzyme assays (5 µM compound). We prepared calibration curves of CTLAP and sc-3136 in cathepsin buffer, pH 5.0 (FIG. 7). From 0-16 µM a good linear increase in absorbance was observed for both sc-3136 ($R^2$=0.9781) and CTLAP ($R^2$=0.9896), suggesting that no significant scattering effects were present in either compound at the concentration used for the enzyme assays. Upon incubation with CTL, both compounds are hydrolyzed to generate the free AMC reporter; we also measured absorbance of AMC from 0-8 µM, and a good fit ($R^2$=0.996) was also determined in this concentration range (data not shown).

We next examined whether another portion of the CTLAP structure absorbs 330 nm light, resulting in an artificially high concentration calculation and a true assay concentration lower than that of sc-3136, resulting in reduced emission intensity. We measured UV-vis absorbance spectra of CTLAP, sc-3136, 3-140, and AMC in DMSO between 250 nm and 400 nm and compared the spectral characteristics of the compounds (FIG. 8). To establish a standard reference point for the absorption curve of caged AMC, we examined the absorption spectrum of sc-3136. The compound exhibits a broad absorbance band with a maximum at 330 nm and a low-energy shoulder peaking around 345 nm. Similarly, CTLAP absorbance shows a local maximum at 330 nm with a similar shoulder at 345 nm. However, another band is present at higher energy, which eclipses that of the caged AMC band. This high-energy band has a maximum at 300 nm and a low-energy shoulder at 315 nm which slopes down into the AMC-regime maximum of 330 nm, still a prominent maximum. As the only prominent structural difference between CTLAP and sc-3136 is the extended benzyl-thiophene group of CTLAP, we examined the absorption spectrum of that moiety alone using compound 3-140 to determine if these new absorption bands in CTLAP were from this portion of the compound. The absorption spectrum of 3-140 shows a single broad curve with a maximum at 290 nm and two near-symmetric, gentle shoulders protruding at 265 nm and 315 nm. Visual comparison with CTLAP absorption supports the conclusion that the higher energy absorption bands in CTLAP come from the benzyl-thiophene structure; thus, the overall absorption of CTLAP is the sum of absorption from caged AMC and the benzyl-thiophene unit. Significantly, the benzyl-thiophene group alone (compound 3-140) shows almost negligible absorption at 330 nm, indicating that this unique structural characteristic of CTLAP should not contribute to the absorption measurements made at this wavelength to calibration the compound concentration, especially not to an extent causing a 6-fold reduction in emission intensity. From this, the absorbance value of CTLAP at 330 nm can be solely attributed to the AMC portion of the compound, meaning the true and calculated concentration of CTLAP in all assay is equivalent to that of sc-3136.

We next tested hypothesis (2), that the emission intensity measured for CTLAP or sc-3136 was somehow compromised by the experimental conditions or by the structural differences of the compounds. The presence of free AMC impurities in either stock solution would increase the emission measured at 445 nm; the presence of hydrolyzed AMC in the stock solution could therefore explain the greater emission intensity observed in the assays. The HPLC traces in FIG. 1 indicate no AMC peak was detected in the assay wells containing CTLAP alone or sc-3136 alone. Also, any free AMC present would augment the intensity observed when exciting at 350 nm more than at 330 nm (as 350 nm is closer to the absorption maximum of AMC); however, the emission intensity ratio between sc-3136 and CTLAP is greater at 330 nm (6.9-fold) than at 350 nm (6.3-fold), suggesting that no AMC impurity is present in sc-3136.

While emission intensity could be influenced by exogenous emitters (such as AMC impurities) present in the solution, this effect could also be produced by the presence of other emitters within the chemical structure of sc-3136. We collected the excitation spectrum of sc-3136 to determine if any other portions of the compound were emitting at 445 nm. We collected emission and excitation spectra of compounds in reaction buffer (pH 5.0) (FIG. 9), and compared them to their respective absorbance spectra (FIG. 8).

The emission spectrum of sc-3136 (FIG. 9A) showed a single curve with the expected maximum at 390 nm for caged AMC and a slight shoulder at 415 nm. As all cathepsin assays were detected at 445 nm emission, we collected the excitation spectrum of sc-3136 centered at this wavelength, scanning an excitation range of 250-400 nm (FIG. 9B). The resulting excitation spectrum had the same shape as that of the absorption spectrum of the compound; as the absorption band of sc-3136 is attributed exclusively to caged AMC, this excitation data supports the conclusion that only the caged AMC portion of sc-3136 contributes to the emission intensity measured at 445 nm, and the higher background intensity is not caused by other portions of the molecule.

We also collected excitation and emission spectra for CTLAP (FIG. 9C, D); the emission profile was identical to that of sc-3136, albeit at lower intensity. The excitation spectrum of CTLAP showed two peaks at 300 nm and ~330 nm, diverging from the excitation and absorption spectra of sc-3136 (caged AMC alone). However, the two peaks in this excitation curve are in alignment with the two peaks observed in the absorption spectrum of the compound: one at 330 nm, attributed to the caged AMC group; and another at 300 nm attributed to the benzyl-thiophene group. This suggests that excitation of the benzyl-thiophene moiety results in emission by CTLAP in the AMC region of 445 nm, possibly by a FRET mechanism. However, this effect should not be observed in the cathepsin assay, as the excitation wavelength used in the assay (350 nm) falls outside the absorption range of 3-140. Regardless, this would result in higher background emission from CTLAP compared to sc-3136, contrary to the lower intensity observed.

In conclusion, the emission and excitation data indicate that emission from sc-3136 can be attributed solely to the caged AMC moiety, and no other emitters are present that could be contributing to the greater background emission intensity observed for the compound.

With data showing that (1) the absorbance of CTLAP is linear near the concentrations used in the assays, and (2) the greater emission of sc-3136 can be attributed completely to the caged AMC moiety, we finally considered whether the lower background intensity of CTLAP was truly a property inherent to its unique chemical structure. The excitation spectrum of CTLAP (FIG. 9D) indicates that the benzyl-thiophene and caged AMC moieties can interact (excitation of benzyl-thiophene results in AMC emission), and we considered that the two moieties may be interacting to reduce the quantum yield of caged AMC in CTLAP. This would lower emission intensity compared to sc-3136, which lacks the benzyl-thiophene group.

To determine quantum yields, standard curves of CTLAP and sc-3136 were constructed between 0-10 μM in buffer, and the absorbance and total emission was measured. Values for the molar attenuation coefficient and quantum yield were standardized using measured absorption and emission intensity of 4-methylumbelliferone (MU) and its literature quantum yield and molar attenuation coefficient[14]. Absorption of the solutions at 350 nm was measured, and all three compounds reported good ($R^2 > 0.96$) linear fit with increasing concentration (FIG. 10A). To measure total emission intensity, the emission spectrum of each compound was collected between 380-600 nm at an excitation wavelength of 350 nm; the area under the emission curve was calculated and graphed as a function of absorption value at 350 nm for each sample (FIG. 10B).

The absorbance of CTLAP increased with a greater slope at higher concentrations than did sc-3136, indicating a larger molar attenuation coefficient. The fluorescence yield of CTLAP was significantly lower than that of sc-3136, though, resulting in a measured quantum yield much lower than that of sc-3136. These results support hypothesis (3), that the unique structure of CTLAP reduces the quantum efficiency of the attached AMC fluorophore, an effect not observed in the simpler structure of sc-3136. The low quantum yield will result in lower emission intensity of CTLAP before activation by CTL, and therefore lower background signal and greater sensitivity when used to detect CTL activity.

TABLE 2[2]

Photophysical properties of compounds

| Compound | $\varepsilon \times 10^{-3}$ | $\phi_F$ |
|---|---|---|
| MU | 19.3 | 0.63 |
| CTLAP | 11.0 | 0.02 |
| sc-3136 | 7.5 | 0.32 |

Table 2. Measured molar attenuation coefficient and quantum yield of CTLAP and sc-3136. Values were standardized against 4-methylumbelliferone (MU).

In conclusion, we report the invention of CTLAP, a fluorogenic probe demonstrating good selectivity for CTL and a significantly reduced background signal. CTLAP exhibits optimal selectivity for CTL within 10 min of incubation time, making it amenable to rapid detection of CTL even in the presence of other cathepsins. CTLAP has a low quantum yield, resulting in higher turn-on ratios than the commercial standard sc-3136, possibly providing high sensitivity for detection of lower levels of CTL. The selectivity and turn-on ratio of CTLAP are better than that of sc-3136 (Z-FR-AMC), a commercially available, standard probe commonly used for fluorogenic detection of CTL activity. These characteristics show CTLAP to be a superior probe for fluorogenic detection of CTL, as CTLAP displays good selectivity for CTL over CTB and CTV while exhibiting low background fluorescence attributed to dual quenching mechanisms.

The development of selective cathepsin probes is challenging due to overlapping substrate selectivity among cathepsins. Detection of CTL activity commonly uses simple fluorogenic substrates such as Z-FR-AMC, however this probe exhibits off-target activation by CTB and other proteases. This type of probe, in which the fluorophore is masked by a substrate sequence or quenching group, can provide high contrast when such groups are removed by the target enzyme. However, its low selectivity often requires inclusion of an exogenous inhibitor or pre-incubation under harsh conditions (4 M urea for 30 min) to deactivate competing enzymes (namely CTB) to achieve selectivity for CTL. A probe with greater selectivity for CTL could eliminate the need for such steps, enabling less intrusive and more convenient real-time detection of CTL activity.

A cathepsin-L activable probe (CTLAP) that experiences dual quenching by its own substrate structure, precluding the need to incorporate exclusive quenching groups in order to enhance emission turn-on (see, e.g., FIG. 1) is advantageous. The probe exhibits a low background signal and over 120-fold turn-on ratio while demonstrating high selectivity for CTL over competing cathepsins within the first 10 min of incubation. These attractive characteristics bridge the gap in current CTL probes, providing a combination of high selectivity and high contrast.

The 120-fold turn-on ratio of CTLAP is attributed to the compounding effect of two quenching mechanisms, the first being a standard off-on mechanism caused by release of AMC, whereas the second is a unique quenching event caused by the 2-phenylthiophene residue that also endows the probe with high selectivity for CTL over competing cathepsins. This could be linked to the effect of adding a quenching dye to the probe to reduce the background of always-on probes (a common strategy for CTL imaging probes) without the need to actually add such a moiety. The idea of probe components (such as a self-immolating aromatic or aliphatic spacer, or reporter and quencher location) influencing selectivity has been demonstrated, but here we show the reverse, that probe components included to increase selectivity can influence the photophysical properties of the probe.

Examples

The invention is further illustrated by the following examples which are intended to illustrate but not limit the scope of the invention.

The compounds of the invention can be evaluated for their cathepsin activity in vitro and in vivo through a variety of assays known in the field. The following examples provide exemplary protocols for evaluating the cathepsin activity of the compounds of the invention.

General Methods

Deuterated solvents were purchased from Sigma-Aldrich and Merck Millipore. $^1$H and $^{13}$C NMR spectra were recorded on a Bruker instrument (500 and 126 respectively) and internally referenced to the residual solvent signals ($^1$H: δ7.26; $^{13}$C: δ77.16 for CDCl$_{13}$, $^1$H: δ3.31; $^{13}$C: δ49.0 for CD$_3$OD respectively). NMR chemical shifts (δ) and the coupling constants (J) for $^1$H and $^{13}$C NMR are reported in parts per million (ppm) and in Hertz, respectively. The following conventions are used for multiplicities: s, singlet; d, doublet; t, triplet; m, multiplet; and dd, doublet of doublet. High resolution mass was recorded on Waters LCT Premier Mass Spectrometer. Absorption spectra were recorded on Shimadzu UV-2700 UV-VIS Spectrophotometer. Fluorescence spectra were recorded on Fluorolog TAU-3 Spectrofluorometer with a xenon lamp (Jobin Yvon-Spex, Instruments S. A., Inc.).

Buffers for cathepsin storage and reaction:

A literature method was consulted[15]: The cathepsin storage buffer was a 100 mM NaOAc/AcOH buffer (pH 5.5), with 2.5 mM DTT and 2.5 mM EDTA, containing 5% v/v glycerol. Two cathepsin reaction buffers were created with identical composition and different pH. The buffers were 100 mM NaOAc/HOAc, 2.5 mM DTT, 2.5 mM EDTA, pH 5.0 or 6.5 (labeled accordingly).

Enzymes, compounds, and reagents: Enzymes were purchased from:
Abcam
 1. Recombinant human Cathepsin L/MEP protein (Active)
   a. Product ab174030; Lot No. (Conc.) GR3210572-1 (N/A)
Sino Biological
 1. Human Cathepsin B/CTSB Protein (His Tag)
   a. Cat. No. 10483-H08H
 2. Human Cathepsin V/Cathepsin L2/Preproprotein Protein (His Tag)
   a. Cat. No. 10093-H08H
 3. Human Cathepsin S/CTSS Protein (His Tag)
   a. Cat. No. 10487-H08H
Santa Cruz Biotechnology, Inc.
 1. Cathepsin L substrate (SC-3136)
AMC was also purchased.

Enzyme storage and preparation:

Enzymes were reconstituted in accordance with manufacturer's instructions. Cathepsin L stock was prepared as described below, to a final concentration of 2.5 uM. Cathepsins B, V, and S were reconstituted in accordance with manufacturer's instructions, then diluted to 2.5 uM in the cathepsin storage buffer (pH 5.5), divided into aliquots, and stored in −80° C. freezer until needed for experiments.

Characterization of probe activation by CTL:

[4-105] Cathepsin L reconstituted as per manufacturer's instructions, then diluted in a preliminary cathepsin storage buffer, in line with a literature procedure[16] (100 mM NaOAc/MaOH, 100 mM NaCl, 10 mM DTT, 1 mM EDTA, pH 5.5). Frozen in −80° C. freezer, and a portion removed and diluted in more cathepsin storage buffer to create 100 nM stock.

Stock solutions of sc-3136 and 3-157 in DMSO prepared to 200 uM (3-157 was less concentrated than this; the value described below was the assumed concentration).

In opaque-bottom 960 well plate, buffer (unfiltered) plated, then probes added, then enzyme added. Final solution in each well was 5 uM probe, 5 nM CTL, 10% DMSO/NaOAc buffer. Incubated at 37° C., removed at 10 min, 30 min, 1 h, and 4 h for measurement on plate reader (Synergy H1). Fluorescence intensity measured at six combinations of literature excitation/emission wavelengths for AMC: Excitation: 340 nm, 360 nm, and 380 nm; Emission: 440 nm, 460 nm. Stored in tin foil at rt for 2 days, then stored in fridge.

From this data, optimum excitation/emission wavelengths determined to be 330 nm/390 nm caged, 350 nm/445 nm activated probe.

To observe probe conversion, a well was diluted with DI water and injected into HPLC. The probe 3-157 ($t_R$=15.57 min) and sc-3136 ($t_R$=15.22 min) peaks were missing, and the same new peak was generated ($t_R$=14.55-14.57 min), consistent with commercial AMC ($t_R$=13.3-13.6 min??). The UV absorption traces of the new product(s) matched that of AMC.

Calibration curve of sc-3136 and 3-157 UV: [4-114]

To standardize concentrations of stock sc-3136 and 3-157 solutions, 200 uM solutions prepared by weighing out >=1 mg solid probe and dissolving in a volume of DMSO to give a 200 uM solution. The solution of sc-3136 was considered more reliable and was standardized as 200 uM. A calibration curve of this compound between 80 uM and 0 uM in 10% PBS/DMSO solutions was prepared. Buffer added to maintain consistent pH and possibly de-quench fluorophore, as DMSO has been shown to quench FITC, another fluorophore. Stock of 3-157 diluted 1:4, 1:5, and 1:8 in same solvent system. UV absorbance at 330 nm (wavelength of max absorption for the caged fluorophore) measured for calibration. A value of 80 uM determined for the 3-157 stock from this curve.

pH Buffer Creation: [4-126]

Buffers from pH 3.0 to 11.0 were created to test fluorophore pH-dependence. Citric acid (0.1 M) and disodium hydrogen phosphate (0.2 M) buffer used for pH 3.0, 4.0, 5.0, and 6.0; disodium hydrogen phosphate (0.2 M) and sodium dihydrogen phosphate (0.2 M) used for pH 7.0 and 8.0; sodium carbonate (0.1 M) and sodium bicarbonate (0.1 M) used for pH 9.0, 10.0, and 11.0.

pH Dependence of AMC Fluorescence: [4-127]

Buffers created to determine if AMC has pH-dependent fluorescence emission. A 50 uM stock of AMC in DMSO was diluted to 5 uM in a well plate, in a final solution of 10% DMSO/buffer. The buffers from pH 3.0 to 11.0 (from 4-126) were used. Plate incubated at 37° C. for 15 min, then read with a BioTek Synergy H1 plate reader to measure emission intensity at 350/445 nm. 3 replicates each, with buffer blanks. No significant change in emission intensity was detected over the pH range 3.0-11.0 for AMC.

To confirm the protocol was set up correctly, the same array was prepared using N3-FITC (DMSO stock from 4-055), one replicate for each pH, and emission measured at 488-518 nm.

Calibration Curve of sc-3136 and 3-157 UV (Repeat): [4-128]

Procedure from 4-114 repeated to ensure correct calibration of probe concentrations. Same materials used, and a stock concentration of 73 uM calculated for 3-157. The sc-3136 was assigned as 200 uM for calibration purposes.

AMC Emission Concentration Calibration Curve: [4-130]

Stock solution of AMC in DMSO diluted between 0.5 uM and 7.5 uM in 10% DMSO/buffer solution using the three cathepsin buffers (pH 5.0, 5.5 storage, and 6.5). Samples were prepared in triplicate, and standard curves were constructed for AMC at each of these three pH values.

Cathepsin Specificity Assay for sc-3136 and 3-157: [4-131]

Enzyme stocks (2.5 uM) were thawed and diluted to 100 nM with cathepsin storage buffer (pH 5.5). From calibrated probe stocks were created 50 uM working stocks in DMSO (3-157 accidentally prepared to 62.5 uM instead). In a 96-well plate, solutions of cathepsin reaction buffer (either pH 5.0 or 6.5), enzyme (5 nM), and probe (5 uM) were prepared. Probe added last to the reaction wells, then read in Synergy H1 plate reader immediately (~5 min) for emission intensity at 350-445 nm. The plate was read at various time points, then stored in fridge overnight but not quenched. The pH 5.0 plate was read again after 48 h to capture completed reaction stage, and to collect emission spectra at 350 nm excitation for both caged and activated compound wells.

To calculate turn-on ratio, the average intensity of the probe-enzyme samples was divided by the average intensity of the background probe samples at the same time point. Total emission intensity was reported as the average emission intensity of the samples at a given time point.

Overall, the intensities of sc-3136 were greater than that of 3-157, both in background and active wells. However, the average absorbance intensity of background probes was equal, suggesting that sc-3136 is inherently more fluorescent than 3-157 when caged—or, rather, 3-157 has lower background fluorescence than sc-3136.

After 48 h, wells A4, A5, E4, and E5 from the pH 5.0 plate had emission spectra measured between 380-500 nm, with excitation set at 350 nm).

UV Spectra of sc-3136, 3-157, 3-140, and AMC: [4-135]

To check if the phenylalanine derivative of 3-157 (and 3-140) could interfere with 330 nm absorbance of caged AMC, these compounds in DMS stocks were diluted in DMSO (concentrations unknown) and UV spectra were measured on a Shimadzu UV-2700 spectrophotometer. The parent phenylalanine derivative (3-140) had almost baseline absorbance at 330 nm. The probe 3-157 had a relative max absorption at this wavelength, due to the caged AMC group. This maximum value was consistent with that of sc-3136, with a notable AMC absorbance shape between 310 nm and 350 nm, peaking at 330 nm. AMC alone had some absorbance at 330 nm, with maximal absorbance at ~355 nm.

UV and fluorescence of 3-157 and sc-3136 stocks: [4-136]

To duplicate unexpected absorbances from 4-131, stocks of probes from 4-128 used to create true 50 uM stocks. UV absorbance at 330 nm measured in a 96-well plate, then 150 uL transferred to an opaque-bottom plate and emission intensity (350/445 nm) was measured. Experiments run in quadruplicate, with a buffer blank. Measured on a BioTek Synergy H1.

The absorbance of 3-157 and sc-3136 were identical, while the emission intensity of 3-157 was 6.1e3 rfu and that of sc-3136 was 4.8e4 rfu, a ratio of 7.8× greater background intensity for sc-3136 over 3-157.

Cathepsin timecourse assay (pH 6.5 and 5.0): [4-138 and 4-139]

Cathepsins reconstituted as usual and diluted into cathepsin reaction buffers (pH 5.0 or 6.5) in an opaque-bottom 96-well plate. Probes added quickly to each active well, then emission measured immediately on BioTek Synergy H1 plate reader, collecting consecutive 36 sec runs over the first 15 min of reaction time. Final probe concentration was 5 uM and final enzyme concentration was 5 nM.

Cathepsin kinetics assay—protocol #1: [4-140]

Cathepsins added to buffer in plate; all enzymes added first. Probe stocks added to a single enzyme set at a time, to make varying final concentration of probe and constant enzyme concentration. Probes were added in order of lowest to highest concentration, then immediately read on a BioTek Synergy H1 plate reader for emission (350/445 nm) intensity, taking data for the first 10-12 min of incubation time. Reaction pH was 5.0; final enzyme concentration was 5 nM; final probe concentration was 1 uM, 1.25 uM, 2 uM, 2.5 uM, or 5 uM.

Cathepsin kinetics assay—protocol #2: [4-142]

A single cathepsin was reconstituted and added to the 96-well plate in all lanes. Probe stocks were diluted, and a single triplicate of probe concentration was added to enzyme and incubated, reading emission for the first 15 min of the reaction. Then, the next highest probe stock was added, the reaction was immediately read for the first 10 min of incubation time in 3 sec intervals. Reaction pH was 6.5; final enzyme concentration was 5 nM; final probe concentration was 1 uM, 1.25 uM, 2 uM, 2.5 uM, or 5 uM. Then, the next cathepsin was reconstituted, added to the plate, and each enzyme concentration was added and measured sequentially in the manner described above.

Cathepsin Kinetics Assay—Protocol #3: [4-143]

Buffer and probes were added to the plate. Single enzyme was reconstituted and added to all active wells, starting with lowest probe concentration and ending with highest probe concentration. Plate immediately read on BioTek Synergy H1 for emission (350-445 nm), every 15 sec for 15 min total. The background probe wells were measured every 30 sec for 2 min to measure background intensity under same instrument settings. The next cathepsin was quickly added to all probe concentrations, then the plate was immediately read again. This process was repeated for all four enzymes.

Spectral Characterization of Compounds [4-174]

Stock solutions of CTLAP, sc-3136, 3-140, and AMC in DMSO were used to prepare 20 uM stocks in DMSO, 200 uL total volume. 50 uL of these solutions were diluted with 150 uL cathepsin L reaction buffer (pH 5.0) to give solutions of 5 uM compound in 25% DMSO/buffer. These samples were used to measure UV-Vis spectra (250-400 nm) on a Shimadzu UV-2700. A blank solution of 25% DMSO/buffer was used to baseline the instrument. Between samples, the cuvette was flushed with 200 uL DMSO, drained, and the next sample was added.

The remaining 150 uL of solution was diluted with 450 uL buffer to give 600 uL of 5 uM compound in 25% DMSO/buffer. The solution was transferred to an opaque-bottom 96-well plate, in three aliquots of 200 uL. The plate was used to measure emission and excitation spectra, and quantitative endpoint emission intensities. All spectral scans were collected at 50 Gain, in 5 nm steps.

Measurement of Molar Absorption Coefficient and Quantum Yield [4-177]

Compounds were compared to 4-methylumbelliferone (4-MU) and 2,4-difluoro-4-methylumbelliferone (DiFMU).

To construct calibration curves, stock solutions of 4-MU and DiFMU were prepared at ~1 mM, then diluted with buffer (carbonate buffer, pH 10) to 50 uM. From these solutions, standard curves were constructed at 50, 25, 10, 5, and 1 uM by dilution with carbonate buffer, pH 10.1. Solutions were plated in 96-well plates. Absorbance at 350 nm was measured, and the fluorescence curve at 350 nm excitation and 380-600 nm was measured. The absorbance at 350 nm was graphed against the area under the curve (AUC) of the fluorescence spectrum from 380-600 nm, and the slope of each line was used to calculate the quantum yield according to the equation:

Absorbance calibration curves of CTLAP and sc-3136, 0-16 µM [4-188]

Stock solutions of CTLAP (3-157) (73 µM in DMSO) and sc-3136 (200 µM in DMSO) were diluted to 2-16 µM with cathepsin reaction buffer (pH 5.0) in a clear-bottom, 96-well plate. Wells containing 100% cathepsin buffer (pH 5.0) were used as background measurements. All samples were created in triplicate. Background absorbance was subtracted from all values, and the resulting absorbance data was graphed as a function of compound concentration.

References

1. Tan, G. J., Peng, Z. K., Lu, J. P. & Tang, F. Q. Cathepsins mediate tumor metastasis. *World J Biol Chem* 4, 91-101, doi:10.4331/wjbc.v4.i4.91 (2013).
2. Olson, O. C. & Joyce, J. A. Cysteine cathepsin proteases: regulators of cancer progression and therapeutic response. *Nat Rev Cancer* 15, 712-729, doi:10.1038/nrc4027(2015).
3. Jakos, T., Pislar, A., Jewett, A. & Kos, J. Cysteine Cathepsins in Tumor-Associated Immune Cells. *Front Immunol* 10, 2037, doi:10.3389/fimmu.2019.02037 (2019).
4. Mohamed, M. M. & Sloane, B. F. Cysteine cathepsins: multifunctional enzymes in cancer. *Nat Rev Cancer* 6, 764-775, doi:10.1038/nrc1949 (2006).
5. Reiser, J., Adair, B. & Reinheckel, T. Specialized roles for cysteine cathepsins in health and disease. *J Clin Invest* 120, 3421-3431, doi:https://doi.org/10.1172/JCI42918 (2010).
6. Abboud-Jarrous, G. et al. Cathepsin L is responsible for processing and activation of proheparanase through multiple cleavages of a linker segment. *J Biol Chem* 283, 18167-18176, doi:10.1074/jbc.M801327200 (2008).
7. Rabelink, T. J. et al. Heparanase: roles in cell survival, extracellular matrix remodelling and the development of kidney disease. *Nat Rev Nephrol* 13, 201-212, doi: 10.1038/nrneph.2017.6 (2017).
8. Legowska, M. et al. Ultrasensitive internally quenched substrates of human cathepsin L. *Anal Biochem* 466, 30-37, doi:10.1016/j.ab.2014.08.010 (2014).
9. Turk, V. et al. Cysteine cathepsins: from structure, function and regulation to new frontiers. *Biochim Biophys Acta* 1824, 68-88, doi:10.1016/j.bbapap.2011.10.002 (2012).
10. Torkar, A., Lenarcic, B., Lah, T., Dive, V. & Devel, L. Identification of new peptide amides as selective cathepsin L inhibitors: the first step towards selective irreversible inhibitors? *Bioorg Med Chem Lett* 23, 2968-2973, doi:10.1016/j.bmcl.2013.03.041 (2013).
11. Chowdhury, M. A. et al. Prodrug-inspired probes selective to cathepsin B over other cysteine cathepsins. *J Med Chem* 57, 6092-6104, doi:10.1021/jm500544p (2014).
12. Nomura, T., Fujishima, A. & Fujisawa, Y. Characterization and crystallization of recombinant human cathepsin L. *Biochem Biophys Res Commun* 228, 792-796, doi:10.1006/bbrc.1996.1733 (1996).
13. Nagler, D. K. et al. Major increase in endopeptidase activity of human cathepsin B upon removal of occluding loop contacts. *Biochemistry* 36, 12608-12615, doi: 10.1021/bi971264+(1997).
14. Sun, W.-C., Gee, K. R. & Haugland, R. P. Synthesis of novel fluorinated coumarins: Excellent UV-light excitable fluorescent dyes. *Bioorganic & Medicinal Chemistry Letters* 8, 3107-3110, doi:10.1016/s0960-894x(98)00578-2 (1998).
15. Bromme, D. Production and activation of recombinant papain-like cysteine proteases. *Methods* 32, 199-206, doi:10.1016/s1046-2023(03)00212-3 (2004).
16. Poreba, M. et al. Selective imaging of cathepsin L in breast cancer by fluorescent activity-based probes. *Chemical Science*, doi:10.1039/C7SC04303A (2018).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

Where ranges are given herein, embodiments are provided in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, embodiments that relate analogously to any intervening value or range defined by any two values in the series are provided, and that the lowest value may be taken as a minimum and the greatest value may be taken as a maximum. Where a phrase such as "at least", "up to", "no more than", or similar phrases, precedes a series of numbers herein, it is to be understood that the phrase applies to each number in the list in various embodiments (it being understood that, depending on the context, 100% of a value, e.g., a value expressed as a percentage, may be an upper limit), unless the context clearly dictates otherwise. For example, "at least 1, 2, or 3" should be understood to mean "at least 1, at least 2, or at least 3" in various embodiments. It will also be understood that any and all reasonable lower limits and upper limits are expressly contemplated where applicable. A reasonable lower or upper limit may be selected or determined by one of ordinary skill in the art based, e.g., on factors such as convenience, cost, time, effort, availability (e.g., of samples, agents, or reagents), statistical considerations, etc. In some embodiments an upper or lower limit differs by a factor of 2, 3, 5, or 10, from a particular value. Numerical values, as used herein, include values expressed as percentages. For each embodiment in which a numerical value is prefaced by "about" or "approximately", embodiments in which the exact value is recited are provided. For each embodiment in which a numerical value is not prefaced by "about" or "approximately", embodiments in which the value is prefaced by "about" or "approximately" are provided. "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. In some embodiments a method may be performed by an individual or entity. In some embodiments steps of a method may be performed by two or more individuals or entities such that a method is collectively performed. In some embodiments a method may be performed at least in part by requesting or authorizing another individual or entity to perform one, more than one, or all steps of a method. In some embodiments a method comprises requesting two or more entities or individuals to each perform at least one step of a method. In some embodiments performance of two or more steps is coordinated so that a method is collectively performed. Individuals or entities performing different step(s) may or may not interact.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound that is CTLAP or salt thereof.
2. A composition comprising a compound of claim 1, or a salt thereof.
3. A method for screening for cathepsin inhibitors, the method comprising:
   a. incubating cathepsin with a test compound;
   b. adding a compound of claim 1, or a salt thereof; and
   c. measuring the fluorescence of the mixture from step b.
4. A method for screening for cathepsin inhibitors, the method comprising:
   a. combining cathepsin, a test compound, and a compound of claim 1, or a salt thereof; and
   b. measuring the fluorescence of the mixture from step a.

5. The method of claim 3, wherein the cathepsin is cathepsin L.

6. The method of claim 4, wherein the cathepsin is cathepsin L.

7. The method of claim 3, further comprising plotting the fluorescence from step c.

8. The method of claim 4, further comprising plotting the fluorescence from step b.

9. A kit comprising a compound of claim 1, or a salt thereof, and instructions for screening test compounds.

10. A kit comprising a compound of claim 1, or a salt thereof, and instructions for screening clinical samples.

11. The kit of claim 9 or 10, further comprising one or more buffers.

12. A method for screening clinical samples, the method comprising:
   a. providing a clinical sample;
   b. combining the sample with a compound of claim 1, or a salt thereof; and
   c. measuring the fluorescence of the mixture from step b.

13. A method for screening clinical samples, the method comprising:
   a. combining the clinical sample and a compound of claim 1, or a salt thereof; and
   b. measuring the fluorescence of the mixture from step a.

14. The method of claim 12 or 13, wherein the sample is urine, saliva, or blood.

15. The method of claim 13, further comprising combining an inhibitor of cathepsin B, V or S.

\* \* \* \* \*